United States Patent [19]

Pfenninger et al.

[11] Patent Number: 4,778,899

[45] Date of Patent: Oct. 18, 1988

[54] PROCESS FOR THE PREPARATION OF PYRROLO (3,4-C) PYRROLES

[75] Inventors: Johannes Pfenninger, Marly; Abul Iqbal, Ettingen; Alain C. Rochat, Fribourg; Olof Wallquist, Marly, all of Switzerland

[73] Assignee: Ciba-Geigy Corporation, Ardsley, N.Y.

[21] Appl. No.: 2,354

[22] Filed: Jan. 12, 1987

Related U.S. Application Data

[62] Division of Ser. No. 793,866, Nov. 1, 1985, Pat. No. 4,659,775.

[30] Foreign Application Priority Data

Nov. 7, 1984 [CH] Switzerland ................ 5336/84

[51] Int. Cl.$^4$ ............................................ C07D 487/04
[52] U.S. Cl. ..................................... 548/453; 546/271
[58] Field of Search .......................................... 548/453

[56] References Cited

U.S. PATENT DOCUMENTS

| | | | |
|---|---|---|---|
| 4,490,542 | 12/1984 | Iqbal et al. | 548/453 |
| 4,579,949 | 4/1986 | Rochat et al. | 548/453 |
| 4,613,669 | 9/1986 | Cassar et al. | 548/453 |

OTHER PUBLICATIONS

D. G. Farnum et al., Tetrahedron Letters 29, 2549 (1974).

Primary Examiner—Glennon H. Hollrah
Assistant Examiner—D. B. Springer
Attorney, Agent, or Firm—Luther A. R. Hall

[57] ABSTRACT

The invention relates to a process for the preparation of pyrrolo[3,4-c]pyrroles of formula (1)

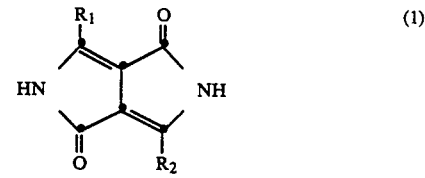

wherein each of $R_1$ and $R_2$ independently of the other is an alkyl or aralkyl group or an isocyclic or heterocyclic aromatic radical, which process comprises reacting an ester of formula (2) or (3)

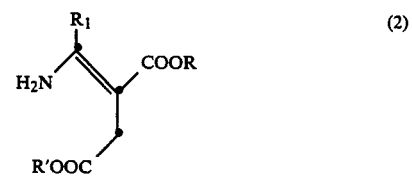

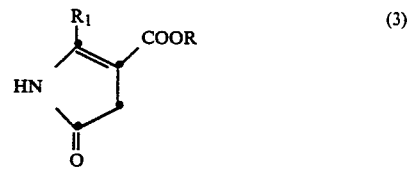

with a nitrile of the formula $R_2CN$, in which formulae each of R and R' independently of the other is an alkyl or aryl group, and $R_1$ and $R_2$ are as defined above, in the presence of a strong base in an organic solvent.

The invention also relates to compounds of formula (8)

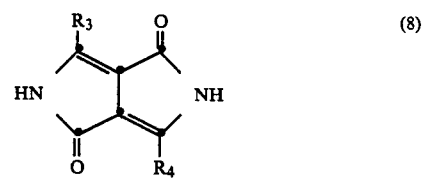

wherein $R_3$ is an alkyl or aralkyl group or an ortho-substituted isocyclic or heterocyclic aromatic radical and $R_4$ is an alkyl or aralkyl group or an isocyclic or heterocyclic aromatic radical.

The pyrrolopyrroles obtained are valuable pigments for coloring compounds of high molecular weight such as plastics and lacquers in yellow to red shades of excellent fastness properties.

4 Claims, No Drawings

PROCESS FOR THE PREPARATION OF PYRROLO (3,4-C) PYRROLES

This is a divisional of application Ser. No. 793,866, filed on Nov. 1, 1985, now U.S. Pat. No. 4,659,775, issued Apr. 21, 1987.

The invention relates to a process for the preparation of 1,4-diketopyrrolo[3,4-c]pyrroles of formula (1)

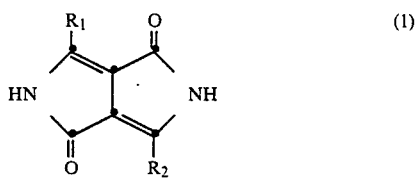

wherein each of $R_1$ and $R_2$ independently of the other is an alkyl or aralkyl group or an isocyclic or heterocyclic aromatic radical, which process comprises reacting an ester of formula (2) or (3)

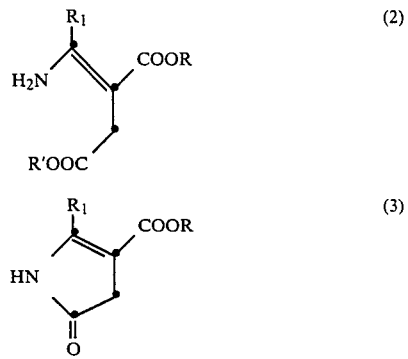

in which formulae $R_1$ is as defined above, each of R and R′ independently of the other is an alkyl, aralkyl or aryl group, with a nitrile of the formula $R_2CN$ (4), wherein $R_2$ is as defined above, in the presence of a strong base in an organic solvent.

R, R′, $R_1$ or $R_2$ in formulae (1), (2) and (3) or $R_2$ in formula (4) as alkyl groups may be branched, unbranched or cyclic, saturated or unsaturated, and contain preferably 1 to 18, in particular 1 to 12 and most preferably 1 to 6, carbon atoms, e.g. methyl, ethyl, isopropyl, sec-butyl, tert-butyl, tert-amyl, cyclohexyl, octyl, decyl, dodecyl or stearyl.

R or R′ as aryl groups may be in particular phenyl which is unsubstituted or substituted by halogen such as chlorine, $C_1$–$C_6$alkyl such as methyl, ethyl, isopropyl or tert-butyl, or $C_1$–$C_6$alkoxy such as methoxy or ethoxy. Aryl is preferably unsubstituted phenyl.

$R_1$ and $R_2$, R and R′ as aralky groups are preferably those which contain a branched or unbranched alkyl or alkenyl chain containing 1 to 12, preferably 1 to 6 and most preferably 1 to 4, carbon atoms, and contain a preferably mono- to tricyclic, most preferably mono- or bicyclic, aryl radical. Examples of such aralkyl groups are benzyl and phenylethyl.

$R_1$ and $R_2$ as isocyclic aromatic radicals are preferably mono- to tetracyclic, most preferably mono- or bicyclic, radicals, e.g. phenyl, diphenylyl or naphthyl radicals. $R_1$ and $R_2$ as heterocyclic aromatic radicals are preferably mono- to tricyclic radicals. Said radicals may be purely heterocyclic or may be a heterocyclic ring and may contain one or more fused benzene rings, e.g. pyridyl, pyrimidyl, pyrazinyl, triazinyl, furanyl, pyrrolyl, thiophenyl, quinolyl, coumarinyl, benzofuranyl, benzimidazolyl or benzoxazolyl. Both the isocyclic and the heterocyclic aromatic radicals may contain the conventional substituents as cited for example in European published application No. 94 911.

The pyrrolinones of formula (3) are obtained for example by cyclising the compound of formula (2) in the presence of a strong base. The cyclisation is carried out by methods known per se, e.g. with sodium methylate in methanol at reflux temperature.

The amino esters of formula (2) are obtained for example by reacting a disuccinate $R'OOCH_2CH_2COOR$ (5) with a nitrile $R_1CN$, in which formulae R, R′ and $R_1$ are as defined above, in the presence of a strong base and a zinc or magnesium salt, by processes analogous to those described in Chem. Lett. 1982, p. 687 and Tetr. Lett 1982, p. 1597.

The pyrrolinones of formula (3) are also obtained by known methods by cyclising a compound of formula (6)

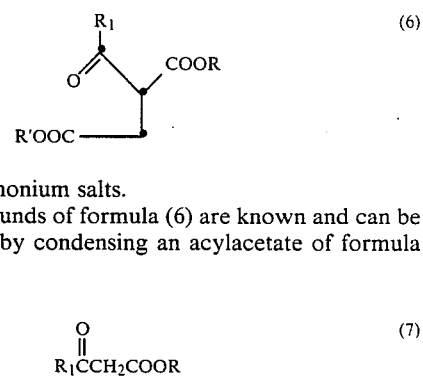

e.g. with ammonium salts.

The compounds of formula (6) are known and can be obtained e.g. by condensing an acylacetate of formula (7)

$$\overset{O}{\underset{}{R_1CCH_2COOR}} \quad (7)$$

wherein $R_1$ and R are as defined above, with an ester of formula $XCH_2COOR'$, wherein X is a fluorine, chlorine, bromine or iodine atom and R′ is as defined above (q.v. W. H. Perkin, J. Chem. Soc. 47, p. 262 or Org. Synth. 42, 75 (1962)).

Examples of starting nitriles to be employed in the process of the present invention are: acetonitrile, propionitrile, butyronitrile, isobutyronitrile, hexyl cyanide, cyclohexyl cyanide, benzyl cyanide, benzonitrile, o-, m- or p-chlorobenzonitrile, o-, m- or p-bromobenzonitrile, o-, m- or p-methylbenzonitrile, p-tertbutylbenzonitrile, p-phenylbenzonitrile, o-, m- or p-methoxybenzonitrile, p-phenoxybenzonitrile, 3,4-dimethylbenzonitrile, isophthalonitrile, terephthalonitrile, 3-pyridyl cyanide or 4-pyridyl cyanide.

The solvents employed in the process of the present invention for the preparation of the pyrrolopyrroles of formula (1) are for example those solvents cited in European published application No. 94 911. Preferred solvents are alcohols, with secondary or tertiary alcohols being most preferred. Preferred tert-alcohols are tert-butanol and tert-amyl alcohol.

The process of this invention is carried out in the presence of a strong base. Examples of suitable strong bases are: alkali metal hydroxide such as sodium, potassium or lithium hydroxide, or alkaline earth metal hydroxides such as calcium or magnesium hydroxide, or alkali metal amides such as lithium amide or lithium diisopropylamide, lithium diethylamide or lithium isopropylcyclohexylamide or sodium amide, or alkali metal hydrides such as lithium hydride or sodium hydride, or alkaline earth metal alcoholates or alkali metal alcoholates which are derived preferably from primary, secondary or tertiary aliphatic alcohols containing 1 to 10 carbon atoms, e.g. sodium, potassium or lithium methylate, sodium, potassium or lithium ethylate, sodium, potassium or lithium n-propylate, sodium potassium or lithium isopropylate, sodium, potassium or lithium n-butylate, sodium, potassium or lithium sec-butylate, sodium, potassium or lithium tert-butylate, sodium potassium or lithium 2-methyl-2-butylate, sodium, potassium or lithium 2-methyl-2-pentylate, sodium, potassium or lithium 3-methyl-3-pentylate, sodium potassium or lithium 3-ethyl-3-pentlyate, or alkaline earth metal phenolates, alkaline earth metal o-alkyl substituted phenolates, alkali metal phenolates or alkali metal o-alkyl substituted phenolates, e.g. sodium or potassium o-cresolate. However, a mixture of the above bases may also be employed.

In the process of this invention preferred strong bases are alkali metal alcoholates, the alkali metal preferably being sodium or potassium and the alcoholate being preferably derived from a secondary or tertiary alcohol. Particularly preferred strong bases are therefore e.g. sodium or potassium isopropylate, sodium or potassium sec-butylate, sodidum or potassium tert-butylate and sodium or potassium tert-amylate. The alkali metal alcoholates may also be prepared in situ by reacting the appropriate alcohol with the alkali metal, alkali metal hydride or alkali metal amide.

In the process of the present invention, the strong base may be employed in an amount of preferably 0.1 to 10 moles, most preferably 0.9 to 4.0 moles, based on 1 mole of the reactant of formula (2) or (3).

The above strong bases may be employed together with a phase transfer catalyst. This is especially advantageous if the solubility of a particular base in a particular solvent is low. The phase transfer catalysts may be employed in an amount of 0.001 to 50 mol%, preferably 0.01 to 0.3 mol%, based on the reactants. Suitable phase transfer catalysts for the process of this invention are the conventional phase transfer catalysts described in the literature, e.g. those listed in CHEMTECH, February 1980, p. 111, Table 1, namely e.g. quaternary salts, cyclic polyethers, open chain polyethers, N-alkylphosphoramides with methylene, bridged phosphorus or sulfur oxides or salts of sulfosuccinates.

The reactions are preferably carried out at a temperature in the range from 60° to 140° C., most preferably from 80° to 120° C.

It is possible to carry out the reactions continuously.

If the solvent employed is an alcohol and the base an alcoholate, it may be advantageous to select an alcohol and an alcoholate containing the same alkyl moieties. It may also be of advantage if the ester of formula (2) or (3) also contains such alkyl groups.

Depending on the base employed, the pyrrolopyrroles are obtained in the form of their sodium or potassium salts, from which the pyrrolopyrroles can be isolated by hydrolysis.

The hydrolysis of the condensation product may be carried out with an acid, an alcohol containing 1 to 4 carbon atoms, e.g. methanol or ethanol, but preferably with water. Examples of suitable acids are: aliphatic or aromatic carboxylic or sulfonic acids, e.g. formic acid, acetic acid, propionic acid, oxalic acid, benzoic acid or benzenesulfonic acid. Further suitable acids are also mineral acids, e.g. hydrochloric acid, aqueous solutions thereof, as well as carbonic acid, dilute sulfuric acid or dilute phosphoric acid.

The compound of formula (1) precipitates during hydrolysis and can be isolated by filtration.

The invention also relates to compounds of formula (8)

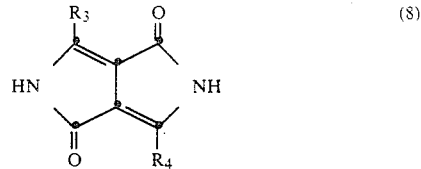

wherein $R_3$ is an alkyl or aralkyl group or an ortho-substituted isocyclic or heterocyclic aromatic radical and $R_4$ is an alkyl or aralkyl group or an isocyclic or heterocyclic aromatic radical, in particular to compounds of formula (8), wherein $R_3$ is a $C_1$-$C_6$alkyl group and $R_4$ is a $C_1$-$C_6$alkyl group or an usubstituted or substituted phenyl or naphthyl radical. Preferred compounds of formula (8) are those wherein $R_3$ is a $C_1$-$C_6$alkyl group and $R_4$ is a radical of the formula

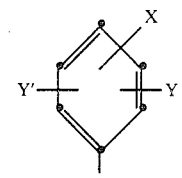

wherein each of X, Y and Y' independently is a hydrogen or halogen atom, a carbamoyl, trifluoromethyl, cyano, $C_2$-$C_6$alkylcarbamoyl, $C_1$-$C_6$alkyl, $C_1$-$C_6$alkoxy, $C_1$-$C_6$alkylmercapto, $C_2$-$C_6$alkoxycarbonyl, $C_2$-$C_6$alkanoylamino or $C_2$-$C_6$dialkylamino group, or is a phenoxy, phenylmercapto, phenoxycarbonyl, phenylcarbamoyl or benzoylamino group which is unsubstituted or substituted by halogen, $C_1$-$C_6$alkyl or $C_1$-$C_6$alkoxy, at least one of the substituents X, Y and Y' being a hydrogen atom. The substituents X, Y and Y' are for example in ortho-, meta- or para-position, preferably in meta- or para-position, to the diketopyrrolopyrrole group.

Particularly preferred compounds of formula (8) are those wherein $R_3$ is a $C_1$-$C_6$alkyl group and $R_4$ is a radical of the formula

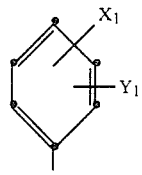

wherein one of the substituents $X_1$ and $Y_1$ is a hydrogen, chlorine or bromine atom, a methyl, cyano, N,N-dimethylamino, N,N,diethylamino, $C_1$-$C_6$alkoxy, $C_2$-$C_4$alkoxycarbonyl or $C_2$-$C_4$alkylcarbamoyl group, or a phenylcarbamoyl group which is unsubstituted or substituted by chlorine, methyl or methoxy, and the other substituent is a hydrogen atom. $X_1$ and $Y_1$ are for example in ortho-, meta- or para-position, preferably in meta- or para-position, to the diketopyrrolopyrrole group.

The compounds of formula (8) are valuable pigments which can be used for colouring organic material of high molecular weight.

Depending on the end use, the pigments obtained by the process of the invention can be converted into a more opaque or more transparent form. To obtain a transparent form, the hydrolysis is preferably carried out at lower temperatures (below 80° C.).

If it is desired to obtain a more opaque pigment form, it is convenient to carry out a hydrolysis at more elevated temperature (above 80° C.), with or without pressure. It is also possible first to isolate the pigment after the hydrolysis and then to heat it in water or an organic solvent, with or without pressure, in order to obtain the opaque form. It is preferred to employ an organic solvent having a boiling point above 80° C. Particularly suitable solvents are benzenes which are substituted by halogen atoms or by alkyl or nitro groups, e.g. xylenes, chlorobenzene, o-dichlorobenzene or nitrobenzene, as well as pyridine bases such as pyridine, picoline or quinoline, and also ketones such as cyclohexanone, ethers such as ethylene glycol monomethyl or monoethyl ether, amides such as dimethylformamide or N-methylpyrrolidone, and also dimethyl sulfoxide or sulfolane. The aftertreatment may also be carried out in water, with our without pressure, in the presence of an organic solvent and/or with the addition of surface-active compounds.

Depending on the envisaged end use, it may be advantageous to prepare mixtures of compounds of formula (8). This can be done for example by mixing different reaction solutions which have been prepared independently of one another before the hydrolysis, hydrolysing them together and then isolating the resultant mixture of compounds of formula (8). It is also possible to reprecipitate two or more compounds of formula (8) together.

Organic materials of high molecular weight, which may be coloured or pigmented with the compounds of formula (8) are e.g. cellulose ethers and esters such as ethyl cellulose, nitrocellulose, cellulose acetate, cellulose butylate, natural resins or synthetic resins such as polymerisation resins or condensation resins, e.g. aminoplasts, in particular urea/formaldehyde and melamine/formaldehyde resins, alkyd resins, phenolic plastics, polycarbonates, polyolefines, polystyrene, polyvinyl chloride, polyamides, polyurethanes, polyesters, rubber, casein, silicone and silicone resins, individually or in mixtures.

The above organic compounds of high molecular weight, individually or in mixtures, may be in the form of plastics, melts or of spinning solutions, lacquers, paints or printing inks. Depending on the end use, it is advantageous to use the pigments of this invention in the form of toners or formulations. The compounds of formula (8) are employed in an amount of preferably 0.1 to 10% by weight, based on the organic material of high molecular weight to be pigmented.

The colourations obtained, e.g. in plastics, filaments, lacquers or printing inks, have excellent tinctorial strength, good dispersibility, good fastness to overspraying, migration, heat, light and atmospheric influences, as well as good gloss.

The invention is illustrated by the following Examples.

EXAMPLE 1

1.5 g of sodium and 30 mg of the sodium salt of bis-2-ethylhexyl sulfosuccinate are stirred at reflux temperature in 30 ml of tert-amyl alcohol until the reaction is complete. 2.2 g of the pyrrolinone of formula (9)

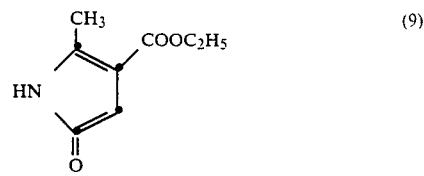

[prepared in accordance with Ann. 260, p. 137 (1890)], dissolved in 20 ml of acetonitrile, are added dropwise to the clear solution, whereupon the reaction temperature drops from 100° to 80° C. After heating for 1 hour at reflux temperature, 15 ml of water are added dropwise and the reaction mixture is cooled to 40° C. The two-phase mixture is taken up in ethyl acetate and acidified with 1N HCl, whereupon yellow crystals precipitate in the aqueous phase. The aqueous phase is separated and filtered and the resultant crystals are washed with methanol and water and dried in vacuo, affording 300 mg (14%) of the compound of formula (10)

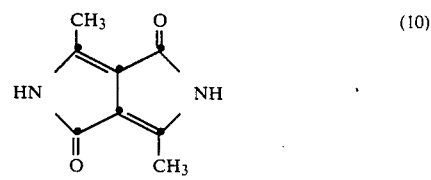

in the form of yellow crystals.

m.p.: >250° C.; UV (CH$_3$OH, $\lambda_{max}$, $\epsilon$) 380(14500), 392(15800).

| $C_8H_8N_2O_2$ | calc.: | C 58.53 | H 4.91 | N 17.06 |
|---|---|---|---|---|
| | found: | C 57.80 | H 5.11 | N 16.81. |

EXAMPLE 2

1 g of sodium and 0.02 g of the sodium salt of bis-2-ethylhexyl sulfosuccinate (emulsifier) are stirred at reflux temperature in 20 ml of tert-amyl until the reaction is complete. To the clear solution are added 3 ml of n-butyronitrile, followed by the addition over 10 minutes of 1 g of the compound of formula (9) in portions. The reaction mixture is boiled for 1 hour under reflux and then cooled to 70° C. A mixture of 5 ml of glacial acetic acid and 7 ml of methanol is added dropwise over 20 minutes. The batch is taken up in ethyl acetate and washed with a concentrated solution of NaCl. The resultant solution is dried over sodium sulfate and then concentrated, whereupon a yellow precipitate forms. The precipitate is isolated by filtration and washed with a small amount of methylene chloride and dried in vacuo, affording the pigment of formula (11)

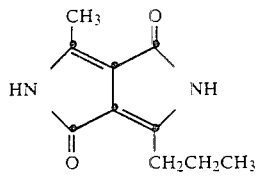
(11)

(270 mg, 24%) which colours PVC yellow.
m.p.: >250° C.
UV, VIS (CH$_3$OH, $\lambda_{max}$, $\epsilon$): 382(12800), 398(14000).

| C$_{10}$H$_{12}$N$_2$O$_2$ | calc.: | C 62.49 | H 6.29 | N 14.57 |
|---|---|---|---|---|
| | found: | C 61.21 | H 6.66 | N 13.41. |

EXAMPLE 3

2 g of sodium and 100 mg of the sodium salt of bis-2-ethylhexyl sulfosuccinate are stirred at reflux temperature until the reaction is complete. The reaction mixture is allowed to cool to 90° C. and 4 g of compound (9) are added. Then 2.5 ml of benzonitrile are added over 30 minutes. The batch is stirred for 1 hour and then neutralised by the dropwise addition of a mixture of acetic acid and methanol. The reaction suspension is cooled to 60° C. and filtered. The filter cake is washed with methanol, water and again with methanol and dried in vacuo, affording the pigment of formula (12)

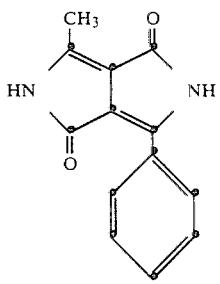
(12)

which colours PVC yellowish brown.
VIS (NMP[1], $\lambda_{max}$, $\epsilon$): 433(12000), 450(10600), 550 (300).
[1]NMP=N-methylpyrrolidone

| C$_{13}$H$_{10}$H$_2$O$_2$ | calc.: | C 69.01 | H 4.46 | N 12.38 |
|---|---|---|---|---|
| | found: | C 68.50 | H 4.47 | N 12.25. |

EXAMPLE 4

400 mg of sodium and 20 mg of the sodium salt of bis-2-ethylhexyl sulfosuccinate are stirred at reflux temperature in 15 ml of tert-amyl alcohol until the reaction is complete. To the clear solution are added 1.58 g of 4-thiophenylbenzonitrile, followed by the addition over 20 minutes of 1.68 g of the pyrrolinone of formula (13)

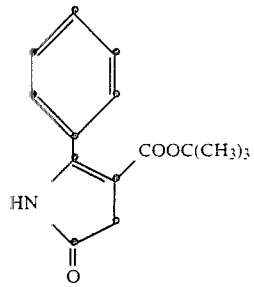
(13)

in small portions. The temperature is kept in the range from 90° to 100° C. The dark red reaction mixture is stirred for 30 minutes at 95° C. and then acidified by the dropwise addition of 8 ml of glacial acetic acid in 20 ml of tert-amyl alcohol. The batch is boiled for a further 1½ hours at 100° C. and then filtered at 70° C. The filter cake is washed with methanol until the washings run colourless, and dried at 60° C. in vacuo, affording 1.47 (74% of theory) of pure pigment of formula (14)

(14)

which colours PVC in red shades.
UV/VIS (in DMF[2], $\lambda_{max}$, $\epsilon$): 350(11500), 480(28400), 518(36800).
[2]DMF=dimethylformamide

| C$_{24}$H$_{16}$N$_2$O$_2$S | calc.: | C 72.71 | H 4.07 | N 7.07 | S 8.09 |
|---|---|---|---|---|---|
| | found: | C 72.06 | H 4.12 | N 7.11 | S 8.01. |

The preparation of the pyrrolidone of formula (13) is described in Example 9.

EXAMPLE 5

The procedure of Example 4 is repeated, using terephthalonitrile instead of 4-thiophenylbenzonitrile and carrying out the reaction at 85° C. The pigment of formula (15)

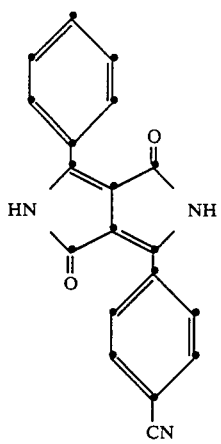

(15)

is isolated in 80% yield. This pigment colours PVC red.

Absorption spectrum in DMF: $\lambda_{max}$ [nm]: 271, 310, 485, 520.

| $C_{19}H_{11}N_3O_2$ | calc.: | C 72.84 | H 3.54 | N 13.41 |
|---|---|---|---|---|
| | found: | C 72.15 | H 3.64 | N 13.40. |

EXAMPLE 6

1.55 g of sodium and 0.02 g of the sodium salt of bis-2-ethylhexyl sulfosuccinate (emulsifier) are stirred at reflux temperature in 27 ml of tert-amyl alcohol until the reaction is complete. To the clear solution are added, at 100° C., 6 g of 4-chlorobenzonitrile, followed by the addition over 30 minutes of 5.1 g of the compound of formula (16)

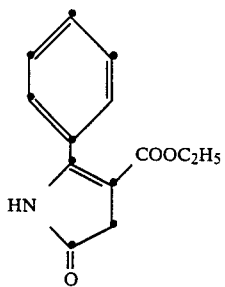

(16)

in portions. The preparation of the compound of formula (16) is described in Example 7.

The reaction mixture is stirred at 100° C. for one hour and then poured into 200 ml of cold water. The mixture is stirred for one hour at reflux temperature and steam is subsequently introduced for one hour in order to remove the organic solvent. The pigment suspension is filtered and the filter cake is dried in vacuo at 80° C., affording 7.2 g (74% of theory) of the pigment of formula (17)

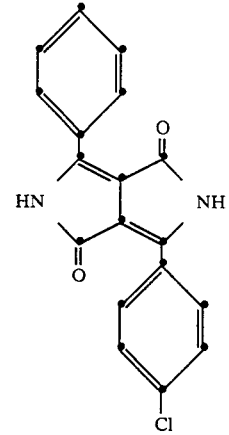

(17)

which colours PVC red.

VIS (NMP, $\lambda_{max}$, $\epsilon$): 471(25300), 510(34100)

| $C_{18}H_{11}N_2O_2Cl$: | calc.: | C 66.98 | H 3.44 | N 8.68 |
|---|---|---|---|---|
| | found: | C 66.92 | H 3.60 | N 8.54. |

EXAMPLE 7

100 g of diethyl benzoylsuccinate and 111 g of ammonium acetate are boiled under reflux in 300 ml of glacial acetic acid for 16 hours. The reaction mixture is poured into 3 liters of cold water. A crystalline precipitate is formed which is isolated by suction filtration and washed with 500 ml of water. The crude product is recrystallised in methylene chloride, affording 48.9 g of the compound of formula (16) in the form of crystals. m.p.: 174° C.

| $C_{13}H_{13}NO_3$ | calc.: | C 67.52 | H 5.67 | N 6.06 |
|---|---|---|---|---|
| | found: | C 67.00 | H 5.71 | N 5.97 |

EXAMPLE 8

In a reaction vessel which has been cooled to −78° C. by a mixture of dry ice and isopropanol, 13.8 ml of a 1.6 molar solution of n-butyl lithium in hexane and 3.1 ml of diisopropylamine are added under a nitrogen atmosphere to 70 ml of anhydrous tetrahydrofuran. After 20 minutes, 2.3 g of di-tert-butyl succinate in 5 ml of tetrahydrofuran are added and the mixture is stirred for 50 minutes. To the reaction mixture are then added 10 ml of a 1 molar solution of zinc chloride in tetrahydrofuran, followed after 30 minutes by the addition of 2.1 g of benzonitrile. After 2 hours, the reaction mixture is allowed to warm to room temperature and is then poured into 200 ml of water. The resultant mixture is taken up in ethyl acetate, the organic phase is washed with a concentrated solution of NaCl and dried over sodium sulfate and the solvent is removed by rotary evaporation. Chromatography over silica gel (elution with an 8:1 mixture of hexane and ethyl acetate) affords 1.96 g (59% of theory, based on the di-tert-butyl succinate) of the compound of formula (18)

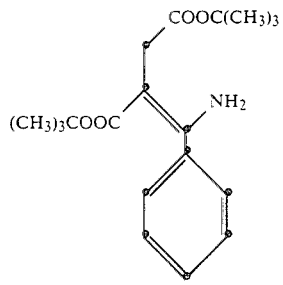

(18)

(or of the corresponding Z isomer) in the form of colourless crystals.

m.p.: 112°–114° C.; (V (CH$_3$OH, $\lambda_{max}$, $\epsilon$): 222(6750), 288(13759).

| C$_{19}$H$_{27}$NO$_4$ | calc.: | C 68.44 | H 8.16 | N 4.20 |
|---|---|---|---|---|
| | found: | C 68.37 | H 8.16 | N 4.21. |

EXAMPLE 9

60 ml of methanol and 30 ml of 30% sodium methylate in methanol are added to 5.03 g of the compound of formula (18) obtained according to Example 8 (or of the corresponding Z isomer) and, under a nitrogen atmosphere, the mixture is heated for 40 minutes to 60° C.

The reaction mixture is poured into ethyl acetate and neutralised with 1N hydrochloric acid and washed with a concentrated solution of NaCl. The organic phase is dried over sodium sulfate and concentrated by rotatry evaporation. Chromatography over silica gel (elution with a 4:1 mixture of toluene and ethyl acetate affords 2.34 g (60% of theory) of the crystalline compound of formula (13)

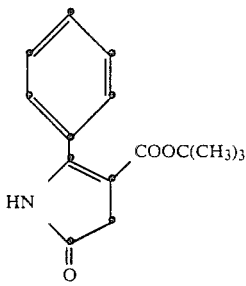

(13)

with a melting point of 153°–154° C.

| C$_{15}$H$_{17}$NO$_3$ | calc.: | C 69.48 | H 6.61 | N 5.40 |
|---|---|---|---|---|
| | found: | C 69.22 | H 6.61 | N 5.32. |

EXAMPLE 10

A suspension of 3.3 g of 3-ethoxycarbonyl-2-phenyl-2-pyrrolin-5-one of formula (16), 2,5 g of 2-chlorobenzonitrile and 3.6 g of potassium tert-butylate in 30 ml of tert-butanol is heated under reflux for 5 hours. The reaction mixture is cooled to room temperature. 50 ml of methanol and then 3.0 ml of glacial acetic acid are added. The pigment suspension is stirred for 5 minutes and then filtered with suction. For purification, the crude pigment is refluxed in 50 ml of methanol for 16 hours, then isolated by suction filtration, washed with methanol and dried in vacuo at 70° C., affording 2.2 g of the pigment of the formula

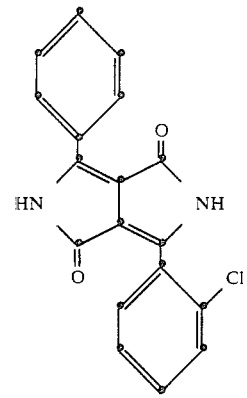

which colours PVC reddish orange.

VIS (NMP, $\lambda_{max}$, $\epsilon$): 459(14700)

| C, H, N-analysis: | C | H | N |
|---|---|---|---|
| found: | 66.66 | 3.60 | 8.65 |

EXAMPLE 11

1.4 g of sodium and 0.03 g of the sodium salt of bis-2-ethylhexyl sulfosuccinate (emulsifier) are stirred at reflux temperature in 20 ml of tert-amyl alcohol until the reaction is complete. To the clear solution are added 1.76 g of lauronitrile, followed by the addition over 5 minutes of 2.0 g of the compound of the formula

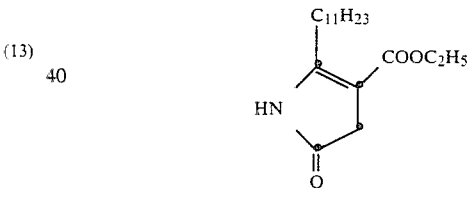

in two portions. The reaction mixture is boiled under reflux for 2 hours and then poured into 100 ml of ice/-water. The mixture is neutralised with 1N HCl and the precipitated pigment is isolated by filtration and washed with water and methanol. The resultant yellow product of the formula is dried in vacuo at 50° C.

m.p.: 247°–250° C.

UV/VIS (NMP $\lambda_{max}$, $\epsilon$), 385(10400), 402(12000)

| C$_{28}$H$_{48}$N$_2$O$_2$ | calc.: | C 75.63 | H 10.88 | N 6.30 |
|---|---|---|---|---|
| | found: | C 75.39 | H 10.73 | N 6.28. |

EXAMPLE 12

The procedure of Example 1 is repeated, using isobutyronitrile (1.5 equivalents) instead of acetonitrile. A yellow pigment of the formula

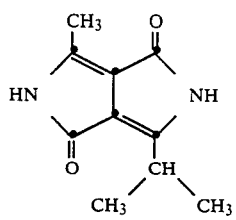

is isolated in a yield of 11%.

UV/VIS (CH$_3$OH, $\lambda_{max}$, $\epsilon$) 383(13400), 397(14800)

| C$_{10}$H$_{12}$N$_2$O$_2$ | calc.: | C 62.49 | H 6.29 | N 14.57 |
|---|---|---|---|---|
| | found: | C 61.76 | H 6.37 | N 14.00. |

EXAMPLE 13

The procedure of Example 1 is repeated, using lauronitrile (2 equivalents) instead of acetonitrile. The yellow pigment of the formula

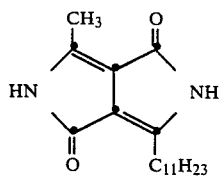

is isolated in a yield of 10%.

UV/VIS (CH$_3$OH, $\lambda_{max}$, $\epsilon$) 382(14750), 398(16250)

| C$_{18}$H$_{28}$N$_2$O$_2$ | calc.: | C 71.02 | H 9.27 | N 9.20 |
|---|---|---|---|---|
| | found: | C 71.11 | H 9.41 | N 9.04. |

EXAMPLE 14

The procedure of Example 6 is repeated, using p-tolunitrile instead of 4-chlorobenzonitrile. A pigment of the formula

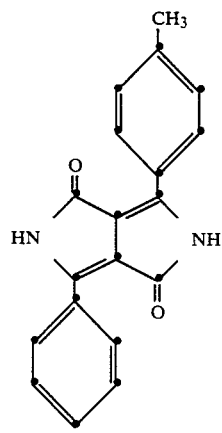

is isolated in 49% yield. This pigment colours PVC red.

UV/VIS (NMP, $\lambda_{max}$, $\epsilon$) 307(14000), 312(14000), 472(26300), 507(35600).

| C$_{19}$H$_{14}$N$_2$O$_2$ | calc.: | C 75.48 | H 4.67 | N 9.27 |
|---|---|---|---|---|
| | found: | C 75.30 | H 4.70 | N 9.23. |

EXAMPLE 15

500 mg of sodium and 20 mg of the sodium salt of bis-2-ethylhexyl sulfosuccinate (emulsifier) are stirred at reflux temperature in 20 ml of tert-amyl alcohol until the reaction is complete. 1.75 ml of butyronitrile are added, followed by the addition over 3 minutes of 1.46 g of the compound of the formula

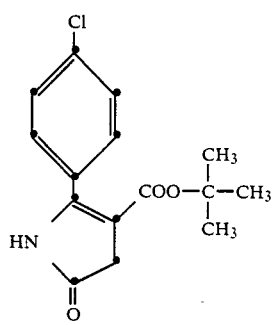

in small portions. The mixture is boiled under reflux for 1 hour and then cooled to 70° C. A mixture of 10 ml of glacial acetic acid and 15 ml of methanol is added dropwise and the batch is stirred for a further hour at 80° C. The precipitated pigment is isolated by filtration, washed with methanol and dried in vacuo at 80° C., affording 750 mg (52% of theory) of a pigment of the formula

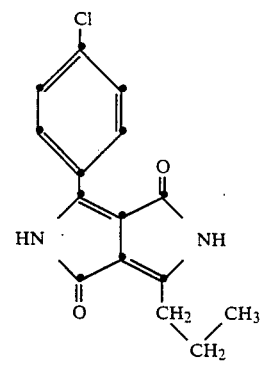

which colours PVC orange.

VIS (DMF, $\lambda_{max}$, $\epsilon$) 460(10200), 510(sh), 630(600)

| C$_{15}$H$_{13}$N$_2$O$_2$Cl | calc.: | C 62.40 | H 4.54 | N 9.70 | Cl 12.28 |
|---|---|---|---|---|---|
| | found: | C 62.28 | H 4.54 | N 9.70 | Cl 12.30. |

EXAMPLE 16

The procedure of Example 15 is repeated, using 4-cyanobiphenyl instead of butyronitrile. The filter cake is dried in vacuo at 60° C., affording the pigment of the formula

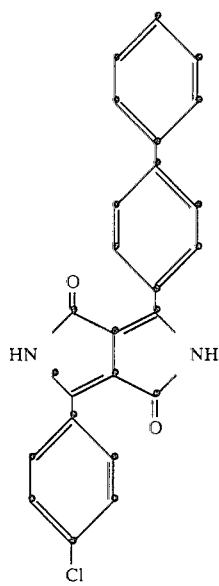

which colours PVC red. Yield: 70% of theory.
UV/VIS (NMP, $\lambda_{max}$, $\epsilon$) 336(16800), 488(31000), 524(40000)

| $C_{24}H_{15}N_2O_2Cl$ | calc.: | C 72.27 | H 3.79 | N 7.02 | Cl 8.89 |
|---|---|---|---|---|---|
| | found: | C 70.54 | H 3.83 | N 6.81 | Cl 8.70. |

EXAMPLE 17

The procedure of Example 15 is repeated, using isophthalonitrile instead of butyronitrile. The crude product is recrystallised in N-methylpyrrolidone, affording a pigment of the formula

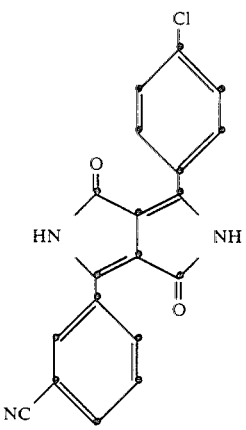

which colours PVC red. Yield: 87% of theory.
UV/VIS (NMP, $\lambda_{max}$ $\epsilon$), 288(14800), 308(14200), 450(sh), 480(23600) 513(31000).

| $C_{19}H_{10}N_3O_2Cl$ | calc.: | C 65.62 | H 2.90 | N 12.08 | Cl 10.19 |
|---|---|---|---|---|---|
| | found: | C 65.11 | H 2.96 | N 11.96 | Cl 10.12. |

EXAMPLE 18

1.7 g of sodium and 0.1 g of the sodium salt of bis-2-ethylhexyl sulfosuccinate (emulsifier) are stirred at reflux temperature in 30 ml of tert-amyl alcohol until the reaction is complete. At 90° C., 5.1 ml of benzonitrile are added, followed by the addition over 10 minutes of 8.95 g of the compound of the formula

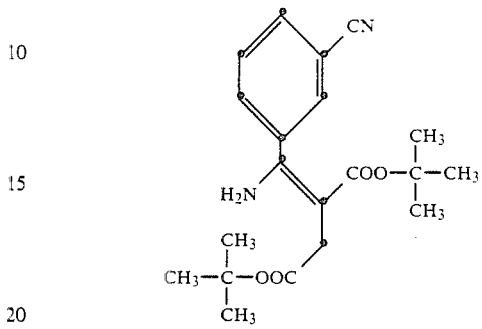

in small portions. The mixture is boiled for 1 hour at 90° C. and then poured into 100 ml of water. After steam distillation lasting 1 hour, the reaction mixture is filtered and the resultant crude product is purified by recrystallisation in dimethylformamide for 5 hours at 120° C. The suspension is cooled and filtered and the filter cake is washed with methanol and water, affording 4.8 g (61% of theory) of a pigment of the formula

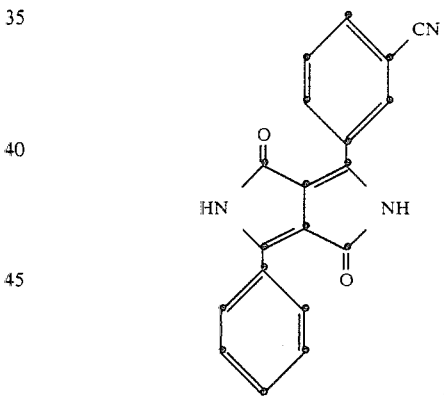

which colours PVC red.
UV/VIS (NMP, $\lambda_{max}$ $\epsilon$) 289(14600), 305(sh), 445(sh), 478(21800) 512(29600).

| $C_{19}H_{11}N_3O_2$ | calc.: | C 72.84 | H 3.54 | N 13.41 |
|---|---|---|---|---|
| | found: | C 72.19 | H 3.65 | N 13.13. |

EXAMPLE 19

The procedure of Example 18 is repeated, using terephthalonitrile instead of benzonitrile. Recrystallisation in N-methylpyrrolidone affords a pigment of the formula

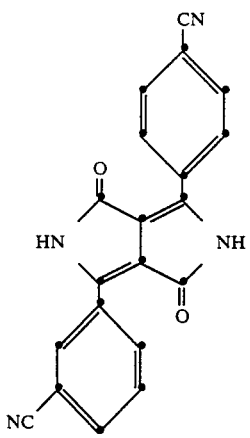

which colours PVC red. Yield: 27%.

UV/VIS (NMP, $\lambda_{max}$, $\epsilon$) 280(31600), 310(sh), 490(20600), 521(24600)

| $C_{20}H_{10}N_4O_2$ | calc.: | C 71.00 | H 2.98 | N 16.56 |
|---|---|---|---|---|
| | found: | C 69.08 | H 3.11 | N 16.03. |

EXAMPLE 20

2.2 g of the compound of formula

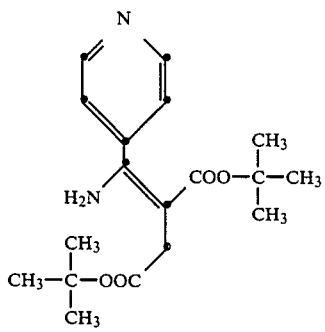

1.8 g of p-chlorobenzonitrile and 2.22 g of potassium tertbutoxide are boiled under reflux in 30 ml of tert-butanol for 2½ hours. The reaction mixture is poured into 150 ml of water. 65 ml of methanol and 25 ml of 1N hydrochloric acid are added and the batch is stirred for 1 hour at room temperature. The crystalline precipitate is washed with water and methanol and dried in vacuo at 60° C., affording 1.6 g (76% of theory, based on the enaminodiester) of red pigment of the formula

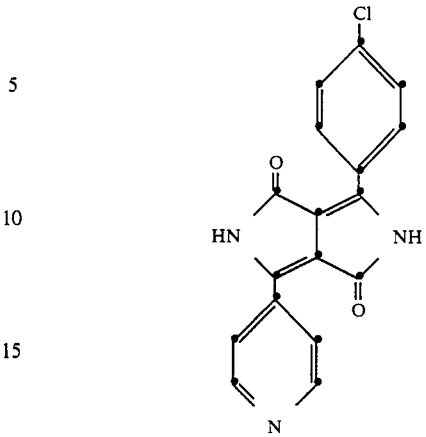

UV/VIS (NMP, $\lambda_{max}$, $\epsilon$) 268(26660), 308(12340), 450(sh), 483(21360), 517(26900).

| $C_{17}H_{10}N_3O_2Cl$ | calc.: | C 63.07 | H 3.11 | N 12.98 |
|---|---|---|---|---|
| | found: | C 62.64 | H 3.33 | N 12.56. |

EXAMPLE 21

72.0 g of potassium tert-butoxide are added to a solution of 64.5 g of 3-ethoxycarbonyl-2-phenyl-2-pyrrolin-5-one of formula (16) and 75.0 g of 9-cyanophenanthrene in 600 ml of tert-butanol and the reaction mixture is stirred for 23 hours at 82° C. The mixture is cooled to 60° C., diluted with 500 ml of methanol and then hydrolysed with 37 ml of acetic acid. The reaction mixture is then cooled and filtered with suction and the filter cake is dried, affording 57.8 g of red powder. The powder is purified by boiling for 3 hours in methanol and is then dried in vacuo at 70° C., affording 48.5 g (39%) of pigment of the formula

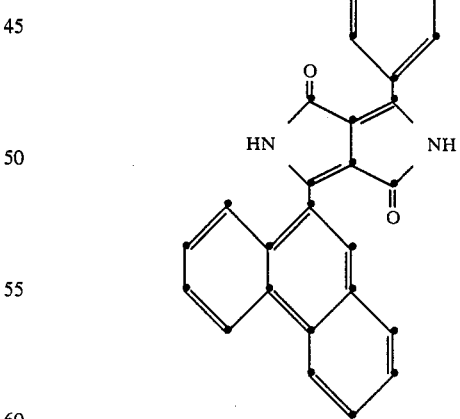

which colours PVC orange.

VIS (NMP, $\lambda_{max}$, $\epsilon$), 472(17200), 492(16800)

| C, H, N analysis | C | H | N |
|---|---|---|---|
| found: | 79.89 | 4.25 | 7.08% |

EXAMPLE 22

In accordance with the procedure described in Example 21, 6.6 g of lactam of formula (16), 5.6 g of 1-naphthonitrile and 10.8 g of potassium tert-butoxide in 60 ml of tert-butanol are stirred under reflux for 5 hours. Conventional working up affords 3.0 g (28%) of pigment of the formula

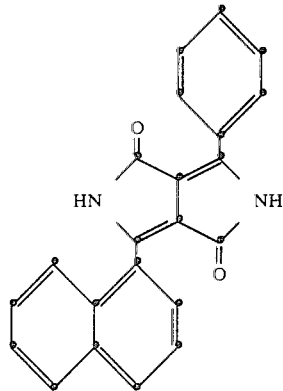

which colours PVC orange.
VIS (NMP, $\lambda_{max}$ $\epsilon$) 470(15800), 493(16300)

| C, H, N analysis | C | H | N |
|---|---|---|---|
| found: | 77.52 | 4.28 | 8.28% |

EXAMPLE 23

In accordance with the procedure described in Example 21, 6.6 g of lactam of formula (16), 6.6 g of 6-methoxy-1-naphthonitrile and 7.1 g of potassium tert-butoxide in 60 ml of tert-butanol are stirred under reflux for 2 hours. Conventional working up affords 0.9 g (2%) of pigment of the formula

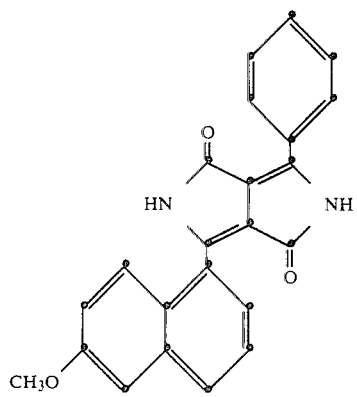

which colours PVC orange.
VIS (NMP, $\lambda_{max}$ $\epsilon$). 500(22600)

| C, H, N analysis | C | H | N |
|---|---|---|---|
| found: | 74.12 | 4.37 | 7.57% |

EXAMPLE 24

In accordance with the procedure described in Example 21, 4.3 g of lactam of formula (16), 2.8 g of o-tolunitrile and 4.8 g of potassium tert-butoxide in 40 ml of tert-butanol are stirred under reflux for 5 hours. Conventional working up affords 0.7 g of pigment of the formula

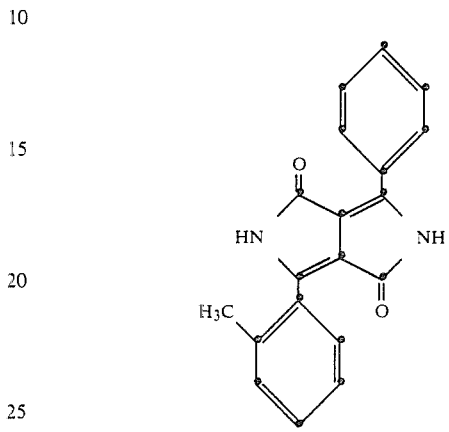

which colours PVC yellowish orange.
VIS (NMP, $\lambda_{max}$, $\epsilon$), 453(19000), 481(21100).

| C, H, N analysis | C | H | N |
|---|---|---|---|
| found: | 73.77 | 4.84 | 8.73% |

EXAMPLE 25

In accordance with the procedure described in Example 21, 4.3 g of lactam of formula (16), 3.4 g of 2,5-dimethylbenzonitrile and 4.8 g of potassium tert-butoxide in 30 ml of tert-butanol are stirred under reflux. Conventional working up affords 0.4 g (6%) of pigment of the formula

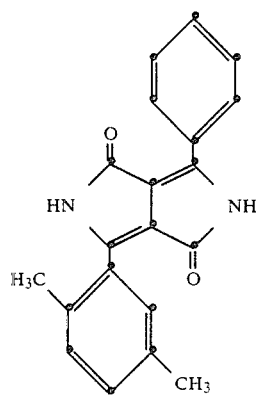

which colours PVC yellow.
VIS (NMP, $\lambda_{max}$ $\epsilon$), 456(18400), 482(20600).

| C, H, N analysis | C | H | N |
|---|---|---|---|
| found: | 74.92 | 5.17 | 8.59% |

EXAMPLE 26

In accordance with the procedure described in Example 21, 3.3 g of lactam of formula (16), 2.1 g of benzyl cyanide and 3.6 g of potassium tert-butoxide in 30 ml of tert-butanol are stirred under reflux for 2 hours. Conventional working up affords 0.8 g (17%) of pigment of the formula

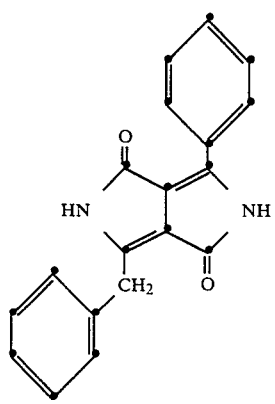

which colours PVC red.

VIS (NMP, $\lambda_{max}$m $\epsilon$) 381(11600), 466(1400).

| C, H, N analysis | C | H | N |
| --- | --- | --- | --- |
| found: | 75.19 | 4.64 | 9.23% |

EXAMPLE 27

In accordance with the procedure described in Example 21, 4.3 g of lactam of formula (16), 3.1 g of 3-phenylpropionitrile and 4.8 g of potassium tert-butoxide in 30 ml of tert-butanol are stirred under reflux for 5 hours. Conventional working up affords 1.0 g of pigment of the formula

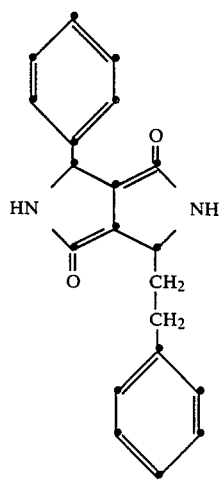

which colours PVC orange.

VIS (NMP), $\lambda_{max}$, $\epsilon$) 438(15800) 459(14600).

| C, H, N analysis | C | H | N |
| --- | --- | --- | --- |
| found: | 75.24 | 5.14 | 8.72%. |

EXAMPLE 28

(Application in soft polyvinyl chloride) 0.6 g of the pigment obtained according to Example 2 is mixed with 67 g of polyvinyl chloride, 33 g of dioctyl phthalate, 2 g of dibutyltin dilaurate and 2 g of titanium dioxide and the mixture is processed to a thin sheet for 15 minutes at 160° C. on a roll mill. The yellow colouration so obtained is strong and exhibits good pigment properties.

EXAMPLE 29

(Application of polyethylene) 0.2 g of the pigment obtained according to Example 10, 1 g of titanium dioxide (rutile) and 100 g of LD polyethylene granules are mixed in a drum and the mixture is then processed on mixer rolls at 130° C. The plastic mass is then pressed hot to sheets or moulded in an extruder. The sheets have a fine red shade of good lightfastness.

EXAMPLE 30

(Application in an alkyd melamine stoving varnish) The following mixture is prepared: 60 g of a 60% solution of a non-drying alkyd resin in xylene (available from Reichhold-Albert-Chemie under the registered trade mark Beckosol 27-320 ®), 36 g of a 50% solution of a melamine/formaldehyd resin in a mixture of butanol and xylene (available from Reichhold-Albert-Chemie under the registered trade name Super-Beckamin 13-501 ®), 2 g of xylene and 2 g of methylcellosolve. 100 g of this mixture are stirred with a stirrer to give a homogeneous varnish solution.

95 g of the clear varnish solution so obtained and 5 g of the pigment obtained according to Example 5 are ground for 72 hours in a ball mill. The coloured varnish solution is then applied to metal by a conventional spraying method and stoved for 30 minutes at 120° C. A red coating of good lightfastness is obtained.

What is claimed is:

1. A process for the preparation of a pyrrolo[3,4-c]pyrrole of formula (1)

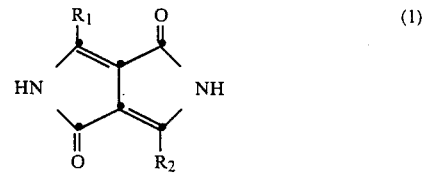

wherein each of $R_1$ and $R_2$ independently of the other is an alkyl or aralkyl group or an isocyclic or heterocyclic aromatic radical, which process comprises reacting an ester of the formula (2) or (3)

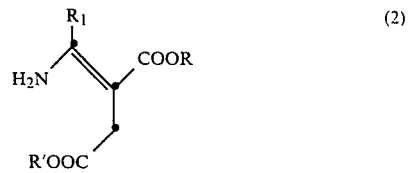

-continued

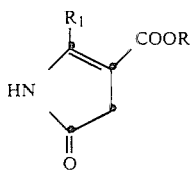

whith a nitrile of the formula R$_2$CN, in which formulae each of R and R' independently of the other is an alkyl or aryl group, and R$_1$ and R$_2$ are as defined above, in the presence of a strong base in an organic solvent.

2. A process according to claim 1, which process comprises starting from an ester and a nitrile of the above formulae, in which R$_1$ and R$_2$ are radicals of the formula

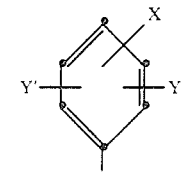

wherein each of X, Y and Y' independently is a hydrogen or halogen atom, a carbamoyl, trifluoromethyl, cyano, C$_2$-C$_6$alkylcarbamoyl, C$_1$-C$_6$alkyl, C$_1$-C$_6$alkoxy, C$_1$-C$_6$alkylmercapto, C$_2$-C$_6$alkoxycarbonyl, C$_2$-C$_6$alkanoylamino or C$_2$-C$_6$dialkylamino group, or is a phenoxy, phenylmercapto, phenoxycarbonyl, phenylcarbamoyl or benzoylamino group which is unsubstituted or substituted by halogen, C$_1$-C$_6$alkyl or C$_1$-C$_6$alkoxy.

3. A process according to claim 1, which comprises starting from an ester of formula (2) or (3), wherein each of R and R' independently of the other is a C$_1$-C$_6$alkyl group.

4. A process according to claim 1, wherein the organic solvent is a sec-alcohol or a tert-alcohol.

* * * * *